(12) United States Patent
Yano et al.

(10) Patent No.: US 8,157,508 B2
(45) Date of Patent: Apr. 17, 2012

(54) BLOWER APPARATUS

(75) Inventors: Takeshi Yano, Kyoto (JP); Akihide Sugawa, Hikone (JP); Atsushi Isaka, Hikone (JP); Fumio Mihara, Kyoto (JP)

(73) Assignee: Panasonic Corporation, Osaka (JP)

( * ) Notice: Subject to any disclaimer, the term of this patent is extended or adjusted under 35 U.S.C. 154(b) by 1009 days.

(21) Appl. No.: 12/120,173

(22) Filed: May 13, 2008

(65) Prior Publication Data

US 2008/0292450 A1 Nov. 27, 2008

(30) Foreign Application Priority Data

May 25, 2007 (JP) .................................. 2007-139494

(51) Int. Cl.
- F04D 29/58 (2006.01)
- F24F 6/12 (2006.01)
- F24F 7/06 (2006.01)

(52) U.S. Cl. ..................... 415/121.3; 236/44 A; 454/337

(58) Field of Classification Search .................. 415/116, 415/121.3; 454/82, 337; 236/44 A, 44 R
See application file for complete search history.

(56) References Cited

U.S. PATENT DOCUMENTS

| | | |
|---|---|---|
| 2006/0104858 A1 | 5/2006 | Potember et al. |
| 2006/0121844 A1* | 6/2006 | Sparks, II ..................... 454/337 |

FOREIGN PATENT DOCUMENTS

| | | |
|---|---|---|
| JP | 4-15059 A | 1/1992 |
| JP | 06-115347 A | 4/1994 |
| JP | 8-224433 A | 9/1996 |
| JP | 2004-50937 A | 2/2004 |
| JP | 2004-173904 A | 6/2004 |
| JP | 2006-61072 A | 3/2006 |
| JP | 2006-151046 A | 6/2006 |
| JP | 2006-205094 A | 8/2006 |
| JP | 2007-137282 A | 6/2007 |
| WO | WO-2005/042171 A1 | 5/2005 |

OTHER PUBLICATIONS

Notification of Reasons for Refusal for the Application No. 2007-139494 from Japan Patent Office mailed Feb. 17, 2009.
European Search Report for the Application No. EP 08 00 8291 dated Sep. 11, 2008.

* cited by examiner

Primary Examiner — Edward Look
Assistant Examiner — Liam McDowell
(74) Attorney, Agent, or Firm — Cheng Law Group, PLLC

(57) ABSTRACT

Blower apparatus has: an air duct having suction and supply openings; a blower fan for creating a flow of air in the duct; and an electrostatic atomizer. The atomizer includes a hollow body exposed to the air in the duct. The body is provided therein with an electrostatic atomization chamber, and has a barrier, an inlet and an outlet. The barrier is put in the duct so that a part of the air flowing in the duct collides with the front of the barrier and thereby pressure-increased air is obtained. The inlet is located at the front side of the barrier so that the pressure-increased air can enter the chamber through the inlet. The outlet is located at the rear side of the barrier so that all the pressure-increased air higher than that of the air flowing in the duct, from the chamber can flow out into the duct.

4 Claims, 3 Drawing Sheets

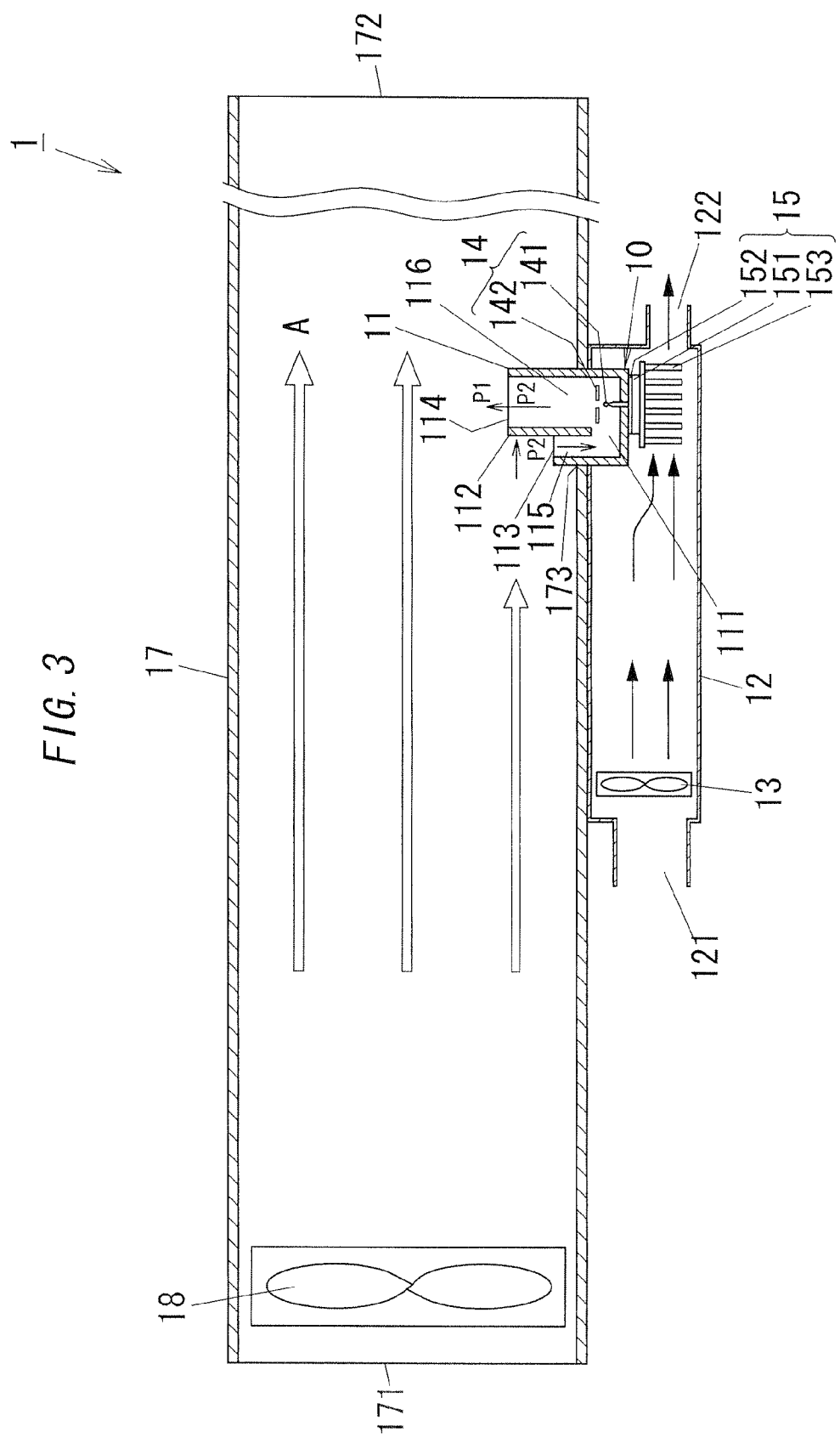

BLOWER APPARATUS

TECHNICAL FIELD

The invention relates generally to blower apparatus and more particularly to blower apparatus equipped with an electrostatic atomizer.

BACKGROUND ART

Conventional various filter air cleaners have been provided in order to remove odor components, allergens and so on. However, the cleaners cannot remove odor components and allergens stuck to interior parts such as dashboard, seats, walls, curtains and so on in an enclosed space such as a vehicle cabin, an indoor space, etc.

Recently attention has been directed to electrostatic atomizers generating mist of charged fine water particles of nanometer-size through electrostatic atomization of water. The mist includes radical such as super oxide radical and hydroxy radical and has effects such as: deodorization effect; elimination (microless) and inhibitory effect of virus and mold; inactivation effect of allergens: and so on. Therefore, the atomizers can remove odor components stuck to said interior parts, and also can inactivate allergens (e.g., pollen) that have stuck to persons or clothes to be brought into said enclosed space.

For example, Japanese Patent Application Publication No. 2006-151046 issued Jun. 15, 2006 discloses blower apparatus (air conditioning apparatus) equipped with an electrostatic atomizer. This atomizer is located in an air duct of the apparatus. The atomizer has a discharge electrode and a counter electrode that are exposed to the air flowing in the air duct. High voltage is applied between the discharge electrode and the counter electrode, and the discharge electrode is periodically supplied with a very small quantity of water (dew drop). Thereby, mist of charged fine water particles is produced through electrostatic atomization, and is carried by the air flowing in the air duct into a vehicle cabin.

However, since a very small quantity of water supplied to the discharge electrode is exposed to the air flowing in the air duct, the water may be blown off by the air flow before the mist is produced by means of electrostatic atomization. Thereby, stable formation of Taylor cone by the water under high voltage is obstructed, so that mist of charged fine water particles cannot be sprayed into the vehicle cabin.

In blower apparatus for a vehicle or central heating system, it is therefore thought that an electrostatic atomizer is located outside an air duct of the apparatus and produces mist of charged fine water particles to supply the mist into the air duct. However, a flow of air in the air duct is created with a blower fan, and therefore the pressure of the air flowing in the air duct is higher than the pressure of the atmosphere. Accordingly, the atomizer located outside the air duct cannot supply the mist into the air duct.

It is therefore thought that the atomizer is further provided with a fan for supplying the mist into the air duct. However, since the fan which can be equipped with the atomizer is inferior to the blower fan in blowing power, the atomizer cannot still supply the mist into the air duct.

It is therefore thought that if a low pressure space exists in the air duct, the atomizer is located at the low pressure space. However, it imposes restrictions on arrangement flexibility of the atomizer. Moreover, when the operation of the blower fan is changed in order to adjust air flow amount of the blower fan, the pressure of the air flowing in the air duct is changed. Accordingly, the atomizer cannot supply the mist into the air duct in same condition. In addition, when the operation of the blower fan is adjusted to maximum, the pressure of the air flowing in the air duct is increased and accordingly it becomes hard to supply the mist into the air duct.

DISCLOSURE OF THE INVENTION

It is an object of the present invention to produce mist of charged fine water particles by stabilized electrostatic atomization to supply the mist into an air duct by simple structure without influence of an air flow in the duct and restrictions on arrangement flexibility of an electrostatic atomizer, and also to stably supply the mist into the duct even if arrangement of the atomizer and the pressure of the air flowing in the duct are changed.

Blower apparatus of the present invention comprises an air duct, a blower fan and an electrostatic atomizer. The air duct has a suction opening and a supply opening. The blower fan is put in the air duct and creates a flow of air from the suction opening to the supply opening. The electrostatic atomizer is configured to produce mist of charged fine water particles by means of electrostatic atomization to spray the mist into the air duct. In an aspect of the invention, the electrostatic atomizer further comprises a hollow body exposed to the air in the air duct. The hollow body comprises an electrostatic atomization chamber, a barrier, an inlet and an outlet. The electrostatic atomization chamber is put in the hollow body, and the mist is produced in the electrostatic atomization chamber. The barrier is put in the air duct so that a part of the air flowing in the air duct collides with the front of the barrier and thereby pressure-increased air is obtained. The inlet is located at the front side of the barrier so that the pressure-increased air can enter the electrostatic atomization chamber through the inlet. Through the outlet, all the pressure-increased air higher than that of the air flowing in the air duct, from the electrostatic atomization chamber can flow out into the air duct.

In this invention, mist of charged fine water particles is produced in the electrostatic atomization chamber without being exposed to the air flow (e.g., rapid air flow) in the air duct. Accordingly, when water is supplied into the electrostatic atomization chamber, it is possible to prevent the water from being blown off by the air flowing in the air duct. The pressure-increased air higher than the air flowing in the air duct flows out into the air duct from the outlet of the hollow body. Accordingly, the atomizer can smoothly supply the air flowing in the air duct with the mist produced in the electrostatic atomization chamber to be carried by the pressure-increased air. Moreover, the pressure of the air supplied from the outlet into the air duct can be made higher than the air flowing in the air duct by the simple structure of the hollow body having the electrostatic atomization chamber, the barrier, the inlet and the outlet. In addition, the pressure-increased air flows out into the air duct by the pressure difference between the pressure-increased air and the pressure of the air flowing in the air duct. Accordingly, the mist can be supplied from the outlet into the air duct by the pressure difference (e.g., a slow flow). Therefore, the atomizer can stably supply the mist into the air duct even if arrangement of the atomizer and the pressure of the air flowing in the duct are changed. If the blower apparatus is used for a vehicle or central heating system, the atomizer can spray the mist on interior parts such as dashboard, seats, walls, curtains and so on in an enclosed space such as a vehicle cabin, an indoor space, etc. In this case, the atomizer can remove or decompose odor components stuck to said interior parts, and also can inactivate allergens that have stuck to persons or clothes to be brought into said enclosed space.

Preferably, the electrostatic atomizer comprises an electrostatic atomization electrode, a water supply means and a high voltage generator. The electrostatic atomization electrode is put in the electrostatic atomization chamber. The water supply means is configured to supply water to the electrostatic atomization electrode. The high voltage generator is configured to apply high voltage to the electrostatic atomization electrode and thereby to apply the high voltage to the water to produce the mist.

Preferably, the outlet is located at the rear side of the barrier.

BRIEF DESCRIPTION OF THE DRAWINGS

Preferred embodiments of the invention will now be described in further details. Other features and advantages of the present invention will become better understood with regard to the following detailed description and accompanying drawings where:

FIG. 3 is a schematic diagram of blower apparatus in an embodiment of the present invention.

BEST MODE FOR CARRYING OUT THE INVENTION

Figure 1:
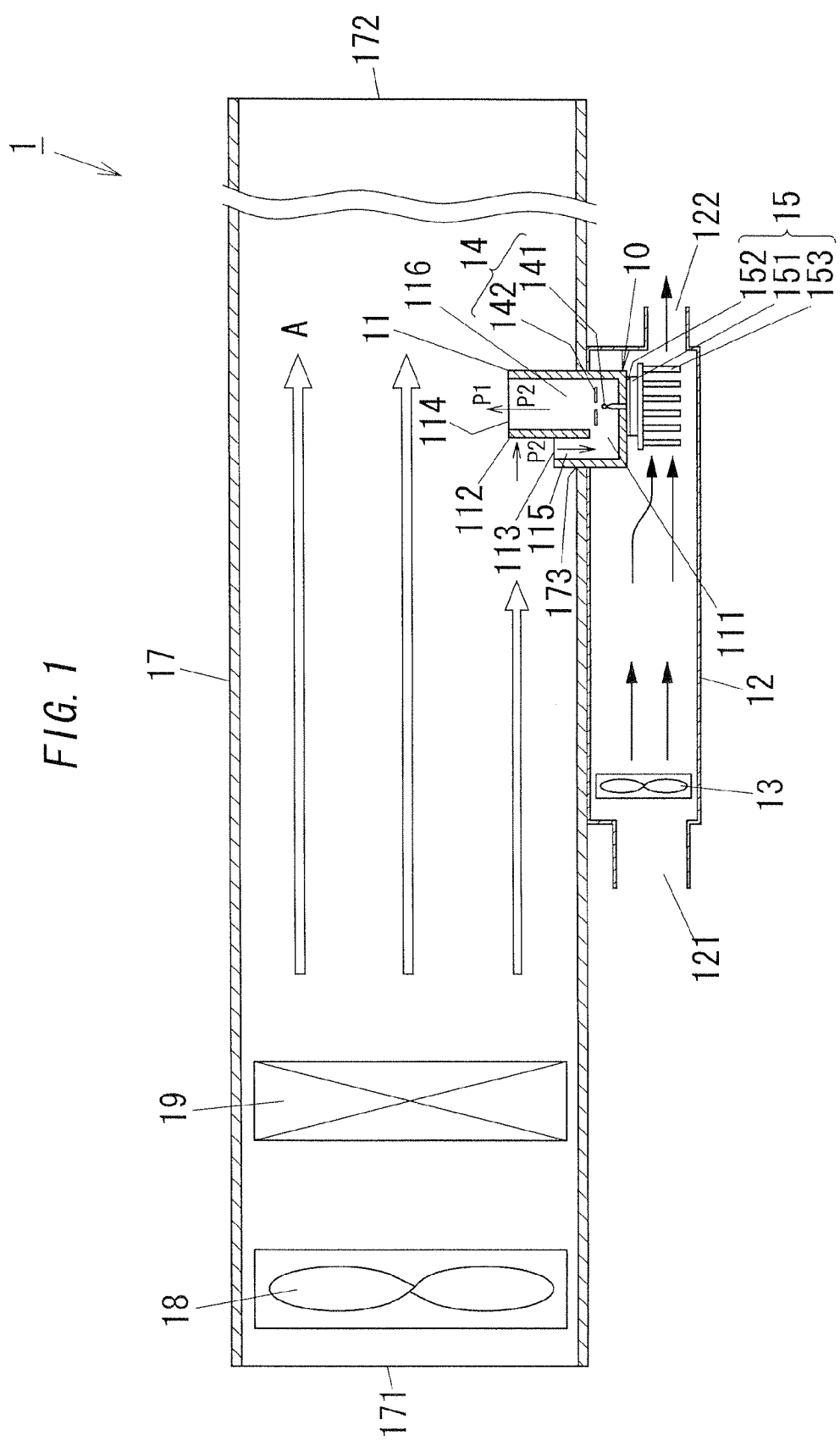
FIG. 1 is a schematic diagram of blower apparatus in accordance with an embodiment of the present invention.

FIG. 1 shows a schematic diagram of blower apparatus 1 in accordance with an embodiment of the present invention. The blower apparatus 1 is utilized for, e.g., a vehicle air conditioner.

The blower apparatus 1 in the vehicle air conditioner has an air duct 17, a blower fan 18, a heat exchanger 19 and an electrostatic atomizer 10.

The air duct 17 has a suction opening 171 and a supply opening 172. The blower fan 18 is put in the air duct 17 and creates a flow of air (A) from the suction opening 171 to the supply opening 172. The blower fan 18 is also located near the suction opening 171. The heat exchanger 19 is located at downstream of the blower fan 18 and also is configured to cool, heat or dry the air from the blower fan 18. For example, an evaporator and a heater are utilized for the heat exchanger 19. The blower fan 18 and the heat exchanger 19 are operated with the vehicle air conditioner. In short, the fan 18 sucks outdoor air or indoor air (vehicle cabin air) through the suction opening 171, and then supplies the conditioned or heated air from the heat exchanger 19 into the vehicle cabin through the supply opening 172.

The electrostatic atomizer 10 is configured to produce mist of charged fine water particles by means of electrostatic atomization to spray (discharge) the mist into the air duct 17. For example, the atomizer 10 is formed of a hollow body 11, an air pipe 12, a cooling fan 13, a high voltage device 14, a cooling means 15 and a controller (not shown).

The hollow body 11 and the air pipe 12 are unified so that the lower part of the hollow body 11 is put in the air pipe 12 made of insulating material. The hollow body 11 may be made of insulating material. The cooling fan 13 is put in the air pipe 12 and creates a flow of air. The hollow body 11 is located near a discharge opening 122 of the air pipe 12, and the cooling fan 13 is located near an intake opening 121 of the air pipe 12. The air pipe 12 is attached outside the air duct 17 while inserting the upper part of the hollow body 11 (the core of the electrostatic atomizer 10) into a hole 173 formed at a voluntary position, e.g., between the heat exchanger 19 and the supply opening 172.

The high voltage device 14 is formed of an I-shaped electrostatic atomization electrode 141, a ring-shaped counter electrode 142, and a high voltage generator (not shown). The electrodes 141 and 142 are arranged opposite each other in the hollow body 11. In the embodiment, the electrode 141 is attached to a hole in the bottom of the hollow body 11, while the electrode 142 is fixed to the inside of the hollow body 11 through an insulator (not shown). The high voltage generator is connected with a power supply including a vehicle battery (not shown), and also configured to be activated with the controller to apply high voltage between the electrodes 141 and 142.

The cooling means (water supply means) 15 is connected with the power supply, and also configured to cool the electrode 141 to produce condensation water (dew drop) on the electrode 141. For example, the cooling means 15 is formed of a Peltier unit 151, a cooling piece 152 and a radiator 153.

The Peltier unit 151 includes two Peltier circuit boards and multiple BiTe thermoelectric elements. Each of the Peltier circuit boards has an insulation board made of material with high thermal conductivity such as alumina or aluminium nitride, and a circuit formed on one side of the insulation board. The Peltier circuit boards are also arranged opposite so that the circuits face to each other. The thermoelectric elements are arranged between the Peltier circuit boards, and the circuits of the boards connect among neighboring thermoelectric elements. The thermoelectric elements are energized through Peltier input lead wires and thereby thermal energy moves from one of the Peltier circuit boards (cooling part) to the other (radiation part). The cooling part is connected with a cooling piece 152, while the radiation part is connected with the radiator 153. In the embodiment, the radiator 153 is a radiation fin unit. The cooling piece 152 is connected with the base of the electrode 141. In order to control electrostatic atomization, the controller controls the cooling fan 13, the high voltage generator of the high voltage device 14, and the Peltier unit 151 of the cooling means 15. The electrode 141, the Peltier unit 151 and so on constitute the core of the electrostatic atomizer 10.

The cooling means 15 is attached to the outside of the bottom of the hollow body 11 and is put in the air pipe 12. Accordingly, the radiator 153 is cooled with the cooling fan 13. The controller, the high voltage generator and so on are put in a storage space(s) divided by partitions (not shown) in the air pipe 12.

The hollow body 11 has an electrostatic atomization chamber 111, a barrier 112, an inlet 113 and an outlet 114. The electrostatic atomization chamber 111 is put in the hollow body 11. The electrodes 141 and 142 are put in the electrostatic atomization chamber 111, and mist of charged fine water particles is produced in the chamber 111. The barrier 112 is put in the air duct 17 so that a part of the air flowing in the air duct 17 collides with the front of the barrier 112 and thereby pressure-increased air (P2) is obtained (produced). The inlet 113 is located at the front side of the barrier 112 so that the pressure-increased air (P2) can enter the electrostatic atomization chamber 111 through the inlet 113. The outlet 114 is located at the rear side of the barrier 112 so that all the pressure-increased air higher than that of the air (P1) flowing in the air duct 17, from the electrostatic atomization chamber 111 can flow out into the air duct 17 through the outlet 114.

Specifically, the electrode 141 projects into the electrostatic atomization chamber 111 from the bottom of the hollow body 11 so that the projection direction of the electrode 141 and the flow direction of air (A) in the air duct 17 cross at given angles (e.g., right angles). The barrier 112 is extended toward the electrostatic atomization chamber 111 through the inlet 113 so that the barrier 112 is arranged in parallel with the projection direction of the electrode 141. Accordingly, the inside of the hollow body 11 is divided into inflow and outflow passages 115 and 116 arranged immediately in front and rear of the barrier 112, respectively. As a result, the inflow passage 115 connected with the inlet 113 is arranged in parallel with the outflow passage 116 connected with the outlet 114, and the electrostatic atomization chamber 111 is arranged between the passages 115 and 116. The opening directions of the inlet 113 and the outlet 114 are in parallel with the projection direction of the electrode 141. Incidentally, the electrostatic atomization chamber 111 may include an area above the inner end of the barrier 112. In short, the electrostatic atomization chamber of the present invention is located between the inlet and the outlet.

The operation of the electrostatic atomizer 10 is now explained. When the atomizer 10 is operated, the Peltier unit 151 is energized and then the cooling piece 152 is cooled with the unit 151. Thereby, the electrode 141 is cooled with the cooling piece 152 and then warm water vapor around the electrode 141 becomes cool, so that condensation water (drop of water) is formed on the electrode 141. Thus, in the condition that the water has been supplied to the electrode 141, high voltage is applied between the electrodes 141 and 142 and then applied to the water supplied to the tip of the electrode 141, and thereby the water supplied on the electrode 141 rises like a cone at the tip of the electrode 141 to form a Taylor cone toward the electrode 142. Subsequently, an electronic charge concentrates on the tip of the Taylor cone, and thereby the Taylor cone further grows by the enhanced electric field at the tip of the Taylor cone. Thus, while the Taylor cone is growing, the electronic charge density at the tip of the Taylor cone is further enhanced, and then large energy (repulsion by the high density of the electronic charge) is added to the water at the tip of the Taylor cone. When the repulsion exceeds the surface tension of the Taylor cone, Rayleigh splitting (split and scatter) occurs. Rayleigh splitting is repeated and thereby mist of negative charged fine water particles that are nanometer in size is produced in large quantities in the electrostatic atomization chamber 111.

In the air duct 17, the blower fan 18 creates a flow of air (A), and accordingly the pressure (P1) of the air flowing in the duct 17 is increased more than the pressure of the atmosphere. On the other hand, the projection direction of the electrode 141 and the flow direction of air (A) in the air duct 17 cross at given angles (e.g., right angles), and the barrier 112 is arranged in parallel with the projection direction. The opening direction of the inlet 113 is also in parallel with the projection direction of the electrode 141. Accordingly, a part of the air flowing in the air duct 17 collides with the front of the barrier 112 and thereby pressure-increased air (P2) in comparison with the air (P1) flowing in the duct 17 is obtained. The pressure-increased air then enters the electrostatic atomization chamber 111 through the inlet 113, and the chamber 111 has the same pressure as the pressure-increased air. Therefore, since the pressure difference P2−P1 (P2>P1) occurs between the outlet 114 and the inside of the air duct 17, the air in the chamber 111 can flow out into the air duct 17 by the pressure difference. Thereby, the mist produced in the chamber 111 is carried by the air flow created by the pressure difference and then is sent into the air duct 17. In short, the pressure P2 in the chamber 111 functions as discharge air pressure for discharging the air in the chamber 111 into the air duct 17.

Thus, the mist is carried by such air flow (e.g., slow air flow) in the chamber 111 without being exposed to the air flow (e.g., rapid air flow) in the air duct 17, and then is sent out. Therefore, it is possible to prevent the water supplied to the electrode 151 from being blown off by the air flowing in the air duct 17. Stable electrostatic atomization can be realized, and the mist can be supplied into the air duct 17.

The core of the electrostatic atomizer 10 can be located at a voluntary position in the air duct 17. Even if the pressure of the air flowing in the air duct 17 is changed by adjusting the blower fan 18, the mist can be sent into the air duct 17. In the same way as the conventional technology, the electrostatic atomizer 10 can spray the mist throughout space (e.g., vehicle cabin), and has advantages such as: deodorization; inactivation of allergens; sterilization; elimination (microless).

Figure 2:
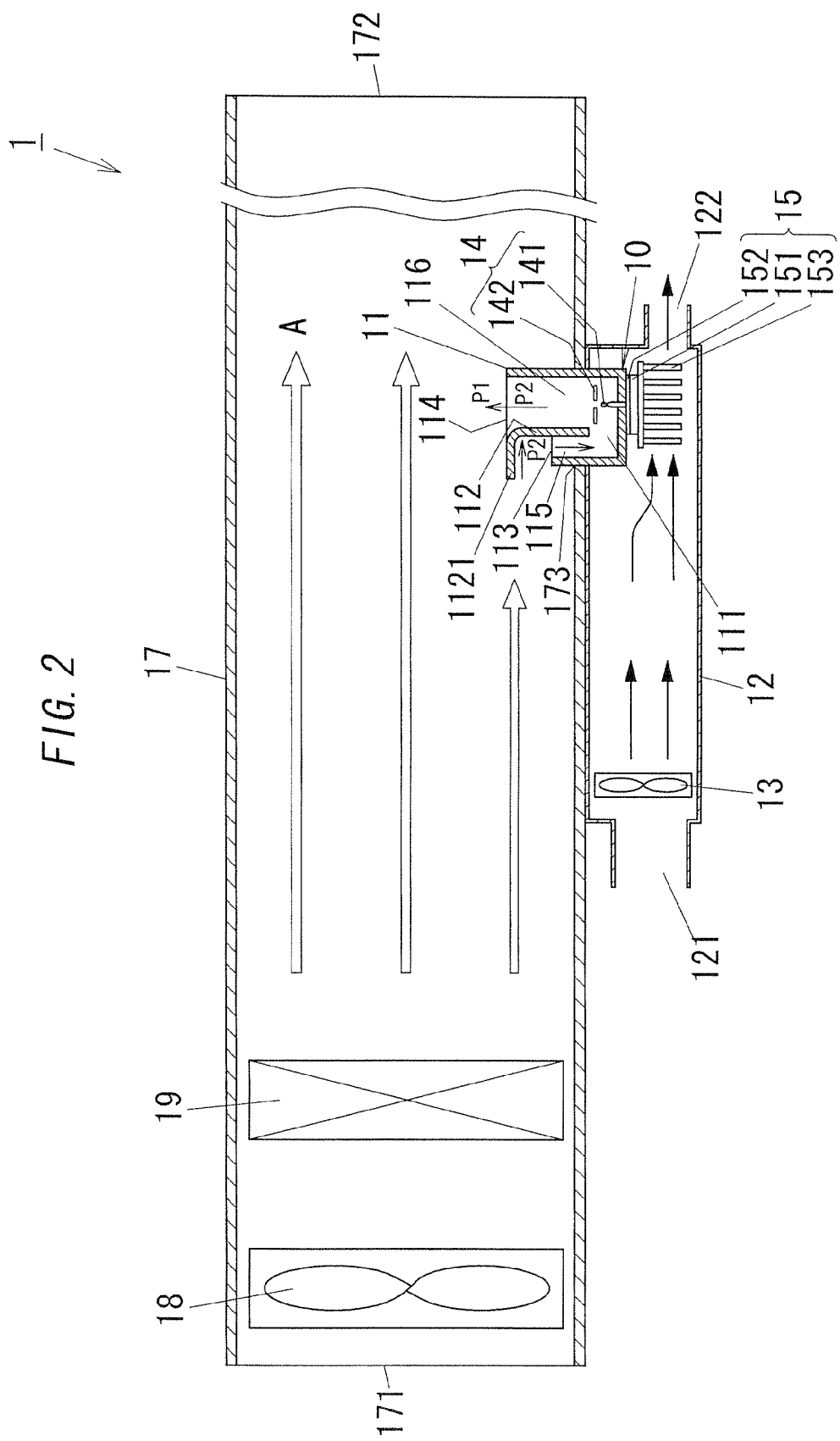
FIG. 2 is a schematic diagram of blower apparatus in an embodiment of the present invention.

In an embodiment, as shown in FIG. 2, a flat-shaped introduction piece 1121 is projected forward from the outer end of the barrier 112. In this case, the pressure-increased air (P2) can effectively enter the electrostatic atomization chamber 111 through the inlet 113.

In an embodiment, as shown in FIG. 3, the blower apparatus 1 has no heat exchanger 19. In this case, the apparatus 1 simply sends air with the blower fan 18.

In an embodiment, the outlet 114 is arranged so that the opening direction of the outlet 114 is directed towards the supply opening 172. In this case, the opening direction of the outlet 114 and the flow direction of air (A) in the air duct 17 may cross, and also the opening direction may be in parallel with the flow direction.

In an embodiment, the blower apparatus 1 is utilized for a central heating and air-conditioning system for a building, or other air-conditioning apparatus.

In an embodiment, all or part of the hollow body 11 (preferably part of the outlet side), which is made of conductive material and is connected with ground and isolated from the electrode 141, is employed instead of the counter electrode 142. In this case, since potential difference occurs between the electrode 141 and the hollow body 11, a Taylor cone toward the hollow body 11 is formed. Similarly, all or part of the air duct 17 (preferably part in front of the electrode 141), which is made of conductive material and is connected with ground and isolated from the electrode 141, may be employed instead of the counter electrode 142. In this case, since potential difference occurs between the electrode 141 and the air duct 17, a Taylor cone toward the air duct 17 is formed.

Although the present invention has been described with reference to certain preferred embodiments, numerous modifications and variations can be made by those skilled in the art without departing from the true spirit and scope of this invention.

The invention claimed is:

1. A blower apparatus, comprising:
   an air duct having a suction opening and a supply opening;
   a blower fan which is put in the air duct and creates a flow of air from the suction opening to the supply opening;
   an electrostatic atomizer configured to produce a mist of charged fine water particles by electrostatic atomization to spray the mist into the air duct;
   wherein the electrostatic atomizer further comprises a hollow body exposed to the air in the air duct,
   said hollow body comprising:
   an electrostatic atomization chamber which is in the hollow body and in which the mist is produced;
   a barrier which is in the air duct so that a part of the air flowing in the air duct collides with a front of the barrier and thereby pressure-increased air is obtained;

an inlet which is located at a front side of the barrier so that the pressure-increased air can enter the electrostatic atomization chamber through the inlet; and an outlet through which all the pressure-increased air higher than that of the air flowing in the air duct, from the electrostatic atomization chamber can flow out into the air duct, wherein the electrostatic atomizer comprises an electrostatic atomization electrode which is in the electrostatic atomization chamber, wherein the electrode projects into the electrostatic atomization chamber from a bottom of the hollow body so that a projection direction of the electrode and a direction of the flow of air in the air duct cross at right angles, and wherein the barrier is extended toward the electrostatic atomization chamber through the inlet so that the barrier is arranged in parallel with the projection direction of the electrode.

2. The blower apparatus of claim 1, wherein the electrostatic atomizer comprises:

a water supply means which is configured to supply water to the electrostatic atomization electrode; and a high voltage generator which is configured to apply high voltage to the electrostatic atomization electrode and thereby to apply the high voltage to the water to produce the mist.

3. The blower apparatus of claim 2, wherein the outlet is located at a rear side of the barrier.

4. The blower apparatus of claim 1, wherein the outlet is located at a rear side of the barrier.

* * * * *